(12) United States Patent
Pikul et al.

(10) Patent No.: US 6,852,751 B2
(45) Date of Patent: Feb. 8, 2005

(54) DIFLUOROBUTYRIC ACID METALLOPROTEASE INHIBITORS

(75) Inventors: Stanislaw Pikul, Germantown, MD (US); Glen Edward Mieling, deceased, late of Germantown, MD (US); by Katherine King Mieling, legal representative, West Chester, OH (US); Kelly Michelle Solinsky, Cincinnati, OH (US); Biswanath De, Cincinnati, OH (US); Neil Gregory Almstead, Holmdel, NJ (US); Michael George Natchus, Alpharetta, GA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/246,179

(22) Filed: Sep. 18, 2002

(65) Prior Publication Data

US 2003/0139453 A1 Jul. 24, 2003

Related U.S. Application Data

(63) Continuation-in-part of application No. PCT/US01/08781, filed on Mar. 20, 2001.
(60) Provisional application No. 60/191,296, filed on Mar. 21, 2000.

(51) Int. Cl.$^7$ .................... A61K 31/405; C07D 209/12; C07D 405/12; C07D 409/12; C07D 411/12

(52) U.S. Cl. .................. 514/414; 514/419; 548/468; 548/494

(58) Field of Search .................... 514/414, 419; 548/468, 494

(56) References Cited

U.S. PATENT DOCUMENTS

| | | |
|---|---|---|
| 4,743,587 A | 5/1988 | Dickens et al. |
| 4,771,038 A | 9/1988 | Wolanin et al. |
| 4,885,283 A | 12/1989 | Broadhurst et al. |
| 4,996,358 A | 2/1991 | Handa et al. |
| 5,006,651 A | 4/1991 | Broadhurst et al. |
| 5,183,900 A | 2/1993 | Galardy et al. |
| 5,300,674 A | 4/1994 | Crimmin et al. |
| 5,318,964 A | 6/1994 | Broadhurst et al. |
| 5,326,760 A | 7/1994 | McElroy et al. |
| 5,387,610 A | 2/1995 | Gray et al. |
| 5,403,952 A | 4/1995 | Hagmann et al. |
| 5,412,145 A | 5/1995 | Crimmin et al. |
| 5,442,110 A | 8/1995 | Isomura et al. |
| 5,447,929 A | 9/1995 | Broadhurst et al. |

(List continued on next page.)

FOREIGN PATENT DOCUMENTS

| | | |
|---|---|---|
| EP | 0 606 046 A1 | 7/1994 |
| EP | 0 575 844 B1 | 1/1998 |
| EP | 0 877 018 A1 | 11/1998 |
| EP | 0 895 988 A1 | 2/1999 |
| EP | 0 950 656 A1 | 10/1999 |
| EP | 0 979 816 A1 | 2/2000 |
| GB | 2 268 934 A | 1/1994 |
| JP | 07-304770 | 11/1995 |
| JP | 08-053403 | 2/1996 |
| WO | WO 92/17460 | 10/1992 |
| WO | WO 93/14112 | 7/1993 |
| WO | WO 94/25435 | 11/1994 |
| WO | WO 95/12603 | 5/1995 |
| WO | WO 95/29892 | 11/1995 |

(List continued on next page.)

OTHER PUBLICATIONS

J. Nemunaitis, et al., "Combined Analysis of Studies of the Effects of the Matrix Metalloproteinase Inhibitor Marimastat on Serum Tumor Markers in Advanced Cancer: Selection of a Biologically Active and Tolerable Dose for Longterm Studies", Clinical Cancer Research, vol. 4, pp. 1101–1109 (1998).

A. E. Yu, et al., "Matrix Metalloproteinases—Novel Targets for Directed Cancer Therapy", Drugs and Aging, vol. 11, No. 3, pp. 229–244 (1997).

J. Bird, et al., "Synthesis of Novel N–Phosphonoalkyl Dipeptide Inhibitors of Human Collagenase", Journal of Medicinal Chemistry, vol. 37, No. 1, pp. 158–169 (1994).

K. Gijbels, et al., "Reversal of Experimental Autoimmune Encephalomyelitis with a Hydroxamate Inhibitor of Matrix Metalloproteases", J. Clin. Invest., vol. 94, pp. 2177–2182 (1994).

B. Henderson, et al., "Design of Inhibitors of Articular Cartilage Destruction", Drugs of the Future, vol. 15, No. 5, pp. 495–508 (1990).

A. F. Chambers, et al., "Changing Views of the Role of Matrix Metalloproteinases in Metastasis", Journal of the National Cancer Institute, vol. 89, No. 17, pp. 1260–1270 (1997).

R. Reich, et al., "Effects of Inhibitors of Plasminogen Activator, Serine Proteinases, and Collagenase IV on the Invasion of Basement by Metastatic Cells" Cancer Research, vol. 48, pp. 3307–3312 (1988).

(List continued on next page.)

Primary Examiner—Taofiq Solola
(74) Attorney, Agent, or Firm—Naishadh N. Desai; David V. Upite

(57) ABSTRACT

Compounds according to the following Formula (I):

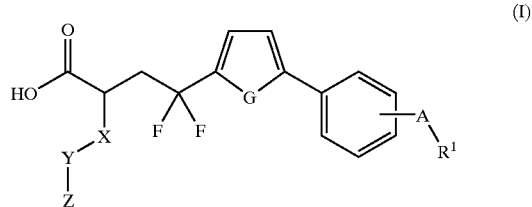

are effective in treating conditions characterized by excess metalloprotease activity.

7 Claims, No Drawings

U.S. PATENT DOCUMENTS

| | | | |
|---|---|---|---|
| 5,470,834 A | | 11/1995 | Schwartz et al. |
| 5,473,100 A | | 12/1995 | Isomura et al. |
| 5,506,242 A | | 4/1996 | MacPherson et al. |
| 5,514,716 A | | 5/1996 | Gowravaram et al. |
| 5,545,735 A | | 8/1996 | Bochis et al. |
| 5,559,129 A | * | 9/1996 | Macor et al. |
| 5,614,625 A | | 3/1997 | Broadhurst et al. |
| 5,616,605 A | | 4/1997 | Gray et al. |
| 5,618,844 A | | 4/1997 | Gowravaram et al. |
| 5,646,167 A | | 7/1997 | MacPherson et al. |
| 5,665,753 A | | 9/1997 | Frazee et al. |
| 5,691,382 A | | 11/1997 | Crimmin et al. |
| 5,698,690 A | | 12/1997 | Broadhurst et al. |
| 5,710,167 A | | 1/1998 | Broadhurst et al. |
| 5,714,491 A | | 2/1998 | Morphy et al. |
| 5,731,441 A | | 3/1998 | Broadhurst et al. |
| 5,747,514 A | | 5/1998 | Beckett et al. |
| 5,763,621 A | | 6/1998 | Beckett et al. |
| 5,773,438 A | | 6/1998 | Levy et al. |
| 5,827,890 A | | 10/1998 | Beeley et al. |
| 5,853,623 A | | 12/1998 | Montana et al. |
| 5,859,253 A | | 1/1999 | Beckett et al. |
| 5,861,436 A | | 1/1999 | Beckett et al. |
| 5,872,152 A | | 2/1999 | Brown et al. |
| 5,886,022 A | | 3/1999 | Kluender et al. |
| 5,892,112 A | | 4/1999 | Levy et al. |
| 5,902,791 A | | 5/1999 | Beckett et al. |
| 5,919,940 A | | 7/1999 | Martin |
| 5,962,529 A | | 10/1999 | Miller et al. |
| 6,017,889 A | | 1/2000 | Beckett et al. |
| 6,022,898 A | | 2/2000 | Miller et al. |
| 6,028,110 A | | 2/2000 | Miller et al. |
| 6,066,662 A | | 5/2000 | Broadhurst et al. |
| 6,093,398 A | | 7/2000 | Khaw et al. |
| 6,114,435 A | | 9/2000 | Nilz et al. |
| 6,124,329 A | | 9/2000 | Miller et al. |
| 6,124,332 A | | 9/2000 | Miller et al. |
| 6,124,333 A | | 9/2000 | Miller et al. |
| 6,166,082 A | | 12/2000 | Kluender et al. |
| 6,225,311 B1 | | 5/2001 | Levin et al. |
| 6,239,288 B1 | | 5/2001 | Purchase, Jr. et al. |
| 6,307,089 B2 | | 10/2001 | Purchase, Jr. et al. |
| 6,379,667 B1 | | 4/2002 | Khaw et al. |
| 2001/0000513 A1 | | 4/2001 | Purchase, Jr. et al. |
| 2002/0164319 A1 | | 11/2002 | Khaw et al. |

FOREIGN PATENT DOCUMENTS

| | | |
|---|---|---|
| WO | WO 95/33731 | 12/1995 |
| WO | WO 96/00214 | 1/1996 |
| WO | WO 97/22587 | 2/1996 |
| WO | WO 98/33768 | 8/1998 |
| WO | WO 98/39329 | 9/1998 |
| WO | WO 99/06340 | 2/1999 |
| WO | WO 99/18079 | 4/1999 |
| WO | WO 99/42443 | 8/1999 |
| WO | WO 99/52889 | 10/1999 |
| WO | WO 00/51993 A3 | 9/2000 |
| WO | WO 00/51993 | 9/2000 |
| WO | WO 00/73294 A2 | 12/2000 |
| WO | WO 00/73295 A1 | 12/2000 |

OTHER PUBLICATIONS

T. G. Wolfsberg, et al., "Adam, a Novel Family of Membrane Proteins Containing A Disintegrin And Metalloprotease Domain: Multipotential Functions in Cell–Cell and Cell–Matrix INteractions", *The Journal of Cell Biology*, vol. 131, No. 2, pp. 275–278 (1995).

H. S. Rasmussen, et al., "Matrix Metalloproteinase Inhibition as a Novel Anticancer Strategy: A Review with Special Focus on Batimastat and Marimastat", *Pharmacol. Ther.*, vol. 75, No. 1, pp. 69–75 (1997).

D. E. Mullins, et al., "The Role of Proteinases in Cellular Invasiveness", *Biochimica et Biophysica Acta.*, vol. 695, pp. 177–214 (1983).

S. R. Bramhall, "The Matrix Metalloproteinases and Their Inhibitors in Pancreatic Cancer", *International Journal of Pancreatology*, vol. 21, No. 1, pp. 1–12 (1997).

J. R. Morphy, et al. "Matrix Metalloproteinases Inhibitors: Current Status", *Current Medicinal Chemistry*, vol. 2, pp. 743–762 (1995).

* cited by examiner

DIFLUOROBUTYRIC ACID METALLOPROTEASE INHIBITORS

CROSS REFERENCE TO RELATED APPLICATIONS

This is a continuation-in-part under 35 U.S.C. § 120 of PCT International Application Ser. No. PCT/US01/08781, filed Mar. 20, 2001; which claims priority to Provisional Application Ser. No. 60/191,296, filed Mar. 21, 2000.

TECHNICAL FIELD

This invention is directed to compounds which are useful in treating diseases associated with metalloprotease activity, particularly zinc metalloprotease activity. The invention is also directed to pharmaceutical compositions comprising the compounds, and to methods of treating metalloprotease-related maladies using the compounds or the pharmaceutical compositions. The invention also relates to novel intermediates useful for the synthesis of the compounds.

BACKGROUND

A number of structurally related metalloproteases effect the breakdown of structural proteins. These metalloproteases often act on the intercellular matrix, and thus are involved in tissue breakdown and remodeling. Such proteins are referred to as metalloproteases or MPs.

There are several different families of MPs, classified by sequence homology, disclosed in the art. These MPs include matrix-metalloproteases (MMPs); zinc metalloproteases; many of the membrane bound metalloproteases; TNF converting enzymes; angiotensin-converting enzymes (ACEs); disintegrins, including ADAMs (See Wolfsberg et al, 131 *J. Cell Bio.* 275–78 October, 1995); and the enkephalinases. Examples of MPs include human skin fibroblast collagenase, human skin fibroblast gelatinase, human sputum collagenase, aggrecanase and gelatinase, and human stromelysin. Collagenases, stromelysin, aggrecanase and related enzymes are thought to be important in mediating the symptomatology of a number of diseases.

Potential therapeutic indications of MP inhibitors have been discussed in the literature. See, for example, U.S. Pat. No. 5,506,242 (Ciba Geigy Corp.) and U.S. Pat. No. 5,403,952 (Merck & Co.); the following PCT published application: WO 96/06074 (British Bio Tech Ltd.); WO 96/00214 (Ciba Geigy), WO 95/35275 (British Bio Tech Ltd.), WO 95/35276 (British Bio Tech Ltd.), WO 95/33731 (Hoffman-LaRoche), WO 95/33709 (Hoffman-LaRoche), WO 95/32944 (British Bio Tech Ltd.), WO 95/26989 (Merck), WO 9529892 (DuPont Merck), WO 95/24921 (Inst. Opthamology), WO 95/23790 (SmithKline Beecham), WO 95/22966 (Sanofi Winthrop), WO 95/19965 (Glycomed), WO 95 19956 (British Bio Tech Ltd.), WO 95/19957 (British Bio Tech Ltd.), WO 95/19961 (British Bio Tech Ltd.), WO 95/13289 (Chiroscience Ltd.), WO 95/12603 (Syntex), WO 95/09633 (Florida State Univ.), WO 95/09620 (Florida State Univ.), WO 95/04033 (Celltech), WO 94/25434 (Celltech), WO 94/25435 (Celltech); WO 93/14112 (Merck), WO 94/0019 (Glaxo), WO 93/21942 (British Bio Tech Ltd.), WO 92/22523 (Res. Corp. Tech Inc.), WO 94/10990 (British Bio Tech Ltd.), WO 93/09090 (Yamanouchi); British patents GB 2282598 (Merck) and GB 2268934 (British Bio Tech Ltd.); published European Patent Applications EP 95/684240 (Hoffman LaRoche), EP 574758 (Hoffman LaRoche) and EP 575844 (Hoffman LaRoche); published Japanese applications JP 08053403 (Fujusowa Pharm. Co. Ltd.) and JP 7304770 (Kanebo Ltd.); and Bird et al., *J. Med. Chem.*, vol. 37, pp. 158–69 (1994).

Examples of potential therapeutic uses of MP inhibitors include: rheumatoid arthritis—Mullins, D. E., et al., *Biochim. Biophys. Acta.* (1983) 695:117–214; osteoarthritis—Henderson, B., et al., *Drugs of the Future* (1990) 15:495–508; cancer—Yu, A. E. et al., *Matrix Metalloproteinases—Novel Targets for Directed Cancer Therapy, Drugs & Aging,* Vol. 11(3), p. 229–244 (September 1997), Chambers, A. F. and Matrisian, L. M., *Review: Changing Views of the Role of Matrix Metalloproteinases in Metastasis, J. of the Nat'l Cancer Inst.,* Vol. 89(17), p. 1260–1270 (September 1997), Bramhall, S. R., *The Matrix Metalloproteinases and Their Inhibitors in Pancreatic Cancer, Internat'l J. of Pancreatology,* Vol. 4, p. 1101–1109 (May 1998), Nemunaitis, J. et al., *Combined Analysis of Studies of the Effects of the Matrix Metalloproteinase Inhibitor Marimastat on Serum Tumor Markers in Advanced Cancer: Selection of a Biologically Active and Tolerable Dose for Longer-term Studies, Clin. Cancer Res.,* Vol 4, p. 1101–1109 (May 1998), and Rasmussen, H. S. and McCann, P. P, *Matrix Metalloproteinase Inhibition as a Novel Anticancer Strategy: A Review with Special Focus on Batimastat and Marimastat, Pharmacol. Ther.,* Vol 75(1), p. 69–75 (1997); the metastasis of tumor cells—ibid, Broadhurst, M. J., et al., European Patent Application 276,436 (published 1987), Reich, R., et al., *Cancer Res.,* Vol. 48, p. 3307–3312 (1988); multiple sclerosis—Gijbels et al., *J. Clin. Invest.,* vol. 94, p. 2177–2182 (1994); and various ulcerations or ulcerative conditions of tissue. For example, ulcerative conditions can result in the cornea as the result of alkali burns or as a result of infection by *Pseudomonas aeruginosa,* Acanthamoeba, Herpes simplex and vaccinia viruses. Other examples of conditions characterized by undesired metalloprotease activity include periodontal disease, epidermolysis bullosa, fever, inflammation and scleritis (e.g., DeCicco et al., World Patent Publication WO 95/29892 published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et al., European Patent Publication No. 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication No. 498,665, published Aug. 12, 1992 by Beckett, et al.; World Patnet Publication No. WO 98/09940, published Mar. 12, 1998 by Purchase et al.

It would be advantageous to inhibit these metalloproteases in treating diseases related to unwanted metalloprotease activity. Though a variety of MP inhibitors have been prepared, there is a continuing need for potent matrix metalloprotease inhibitors useful in treating diseases associated with metalloprotease activity.

SUMMARY OF THE INVENTION

The invention provides compounds which are potent inhibitors of matrix metalloproteases and which are effective in treating conditions characterized by excess activity of these enzymes. In particular, the present invention relates to compounds having a structure according to the following Formula (I):

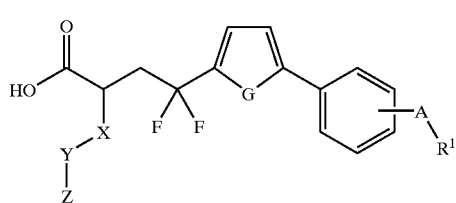

(I)

wherein:
(A) A is selected from a covalent bond, $C_1$–$C_3$ alkyl, O, S, SO, and $SO_2$;
(B) $R^1$ is selected from hydrogen, alkoxy, halogen, —CN, alkyl, alkene, alkyne, heteroalkyl, haloalkyl, aryl, arylalkyl, heteroaryl, heteroarylalkyl, cycloalkyl, cycloalkylalkyl, heterocycloalkyl and heterocycloalkylalkyl;
(C) X is selected from a covalent bond and $C_1$–$C_3$ alkyl optionally substituted with a hydroxy group;
(D) Y is selected from a covalent bond, O, S, SO, $SO_2$ and $NR^2$, wherein $R^2$ is selected from hydrogen, alkyl, alkene, alkyne, heteroalkyl, haloalkyl, aryl, arylalkyl, heteroaryl, heteroarylalkyl, cycloalkyl, cycloalkylalkyl, heterocycloalkyl and heterocycloalkylalkyl;
(E) Z is selected from hydrogen, alkoxy, halogen, —CN, alkyl, alkene, alkyne, heteroalkyl, haloalkyl, aryl, arylalkyl, heteroaryl, heteroarylalkyl, cycloalkyl, cycloalkylalkyl, heterocycloalkyl and heterocycloalkylalkyl; or Z and $R^2$, together with the atoms to which they are bonded, join to form an optionally substituted heterocyclic ring containing from 5 to 8 ring atoms of which 1 to 3 are heteroatoms; and
(F) G is selected from —S—, —O—, —N($R^3$)— and —CH=CH—, where $R^3$ is selected from hydrogen, alkyl, heteroalkyl and acyl.

This invention also includes optical isomers, diastereomers and enantiomers of Formula (I), and pharmaceutically-acceptable salts, or biohydrolyzable esters thereof. This invention also includes intermediates useful for the synthesis of the compounds of Formula (I).

The compounds of the present invention are useful for the treatment of diseases and conditions which are characterized by unwanted metalloprotease activity. Accordingly, the invention further provides pharmaceutical compositions comprising these compounds. The invention still further provides methods of treatment for metalloprotease-related maladies. The invention also encompasses the use of the diflurobutyric acid compounds of this invention to prepare a composition for the treatment of such maladies.

All documents described herein are hereby incorporated by reference.

DETAILED DESCRIPTION OF THE INVENTION

I. Terms and Definitions:

The following is a list of definitions for terms used herein.

"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkene (i.e., —O-alkyl or —O-alkene). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

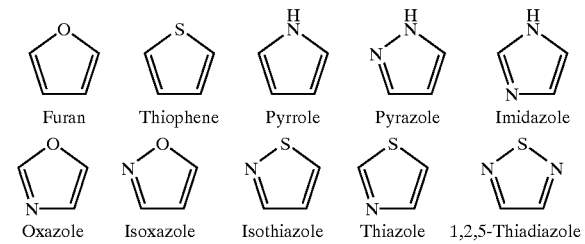

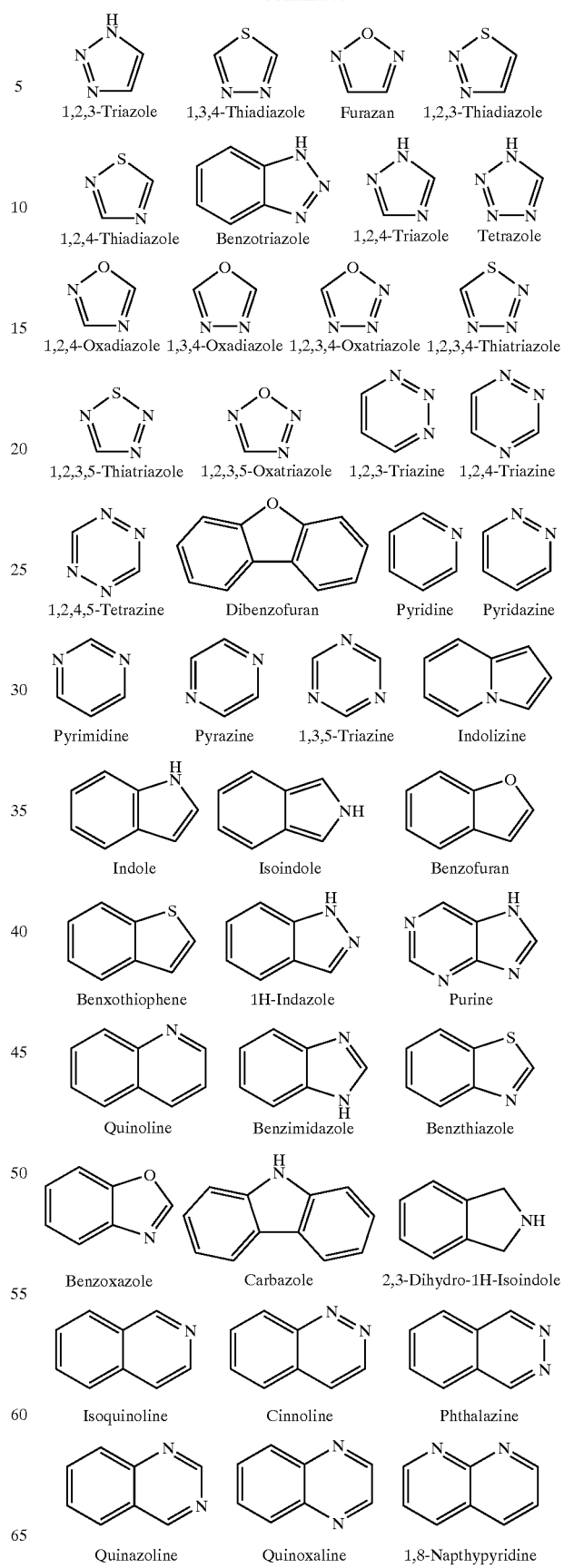

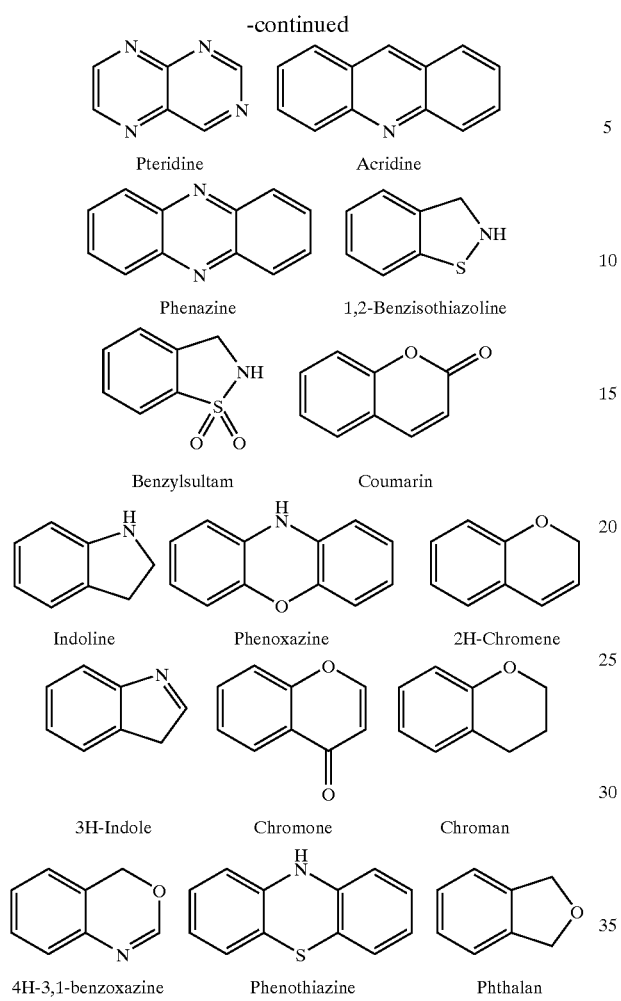

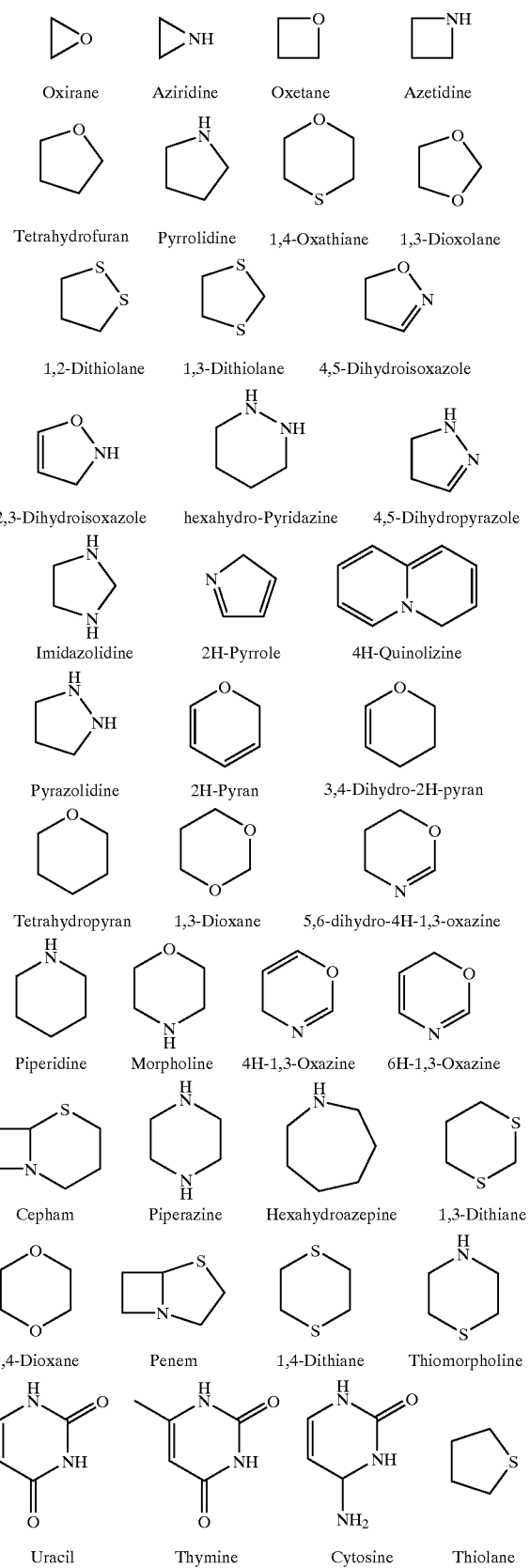

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

As used herein, "mammalian metalloprotease" refers to the proteases disclosed in the "Background" section of this application. The compounds of the present invention are preferably active against "mammalian metalloproteases", including any metal-containing (preferably zinc-containing) enzyme found in animal, preferably mammalian, sources capable of catalyzing the breakdown of collagen, gelatin or proteoglycan under suitable assay conditions. Appropriate assay conditions can be found, for example, in U.S. Pat. No. 4,743,587, which references the procedure of Cawston, et al., Anal. Biochem. (1979) 99:340–345; use of a synthetic substrate is described by Weingarten, H., et al., Biochem. Biophy. Res. Comm. (1984) 139:1184–1187. See also Knight, C. G. et al., "A Novel Coumarin-Labelled Peptide for Sensitive Continuous Assays of the Matrix Metalloproteases", FEBS Letters, Vol. 296, pp. 263–266 (1992). Any standard method for analyzing the breakdown of these structural proteins can, of course, be used. The present compounds are more preferably active against metalloprotease enzymes that are zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

"Spirocycle" is an alkyl or heteroalkyl di-radical substituent of alkyl or heteroalkyl wherein said di-radical substituent is attached geminally and wherein said di-radical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable ester" is an ester of a carboxylic acid-containing metalloprotease inhibitor of the present invention that does not interfere with the metalloprotease inhibitory activity of these compounds or that is readily converted by an animal to yield an active metalloprotease inhibitor. Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

A "solvate" is a complex formed by the combination of a solute (e.g., a metalloprotease inhibitor) and a solvent (e.g., water). See J. Honig et al., The Van Nostrand Chemist's Dictionary, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., Hawley's Condensed Chemical Dictionary, 11th Ed.). The illustration of specific protected forms and other derivatives of the compounds of the instant invention is not intended to be limiting. The application of other useful protecting groups, salt forms, etc. is within the ability of the skilled artisan.

II. Compounds:

The invention provides compounds which are inhibitors of matrix metalloproteases and which are effective in treating conditions characterized by excess activity of these enzymes. In particular, the present invention relates to compounds having a structure according to the following Formula (I):

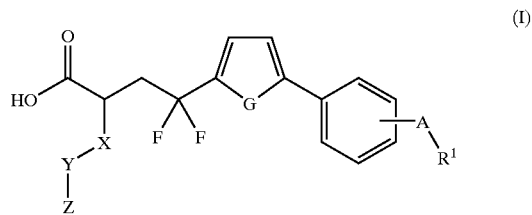

(I)

where $R^1$, A, G, X, Y and Z have the meanings described above. The following provides a description of particularly preferred moieties, but is not intended to limit the scope of the claims.

A is selected from a covalent bond, $C_1$–$C_3$ alkyl, O, S, SO and $SO_2$; preferably A is a covalent bond, O or S.

$R^1$ is selected from hydrogen, alkoxy, halogen, —CN, alkyl, alkene, alkyne, heteroalkyl, haloalkyl, aryl, arylalkyl, heteroaryl, heteroarylalkyl, cycloalkyl, cycloalkylalkyl, heterocycloalkyl and heterocycloalkylalkyl; preferably $R^1$ is hydrogen, alkyl, heteroalkyl or halogen.

X is selected from a covalent bond or $C_1$–$C_3$ alkyl optionally substituted with a hydroxy group.

Y is selected from a covalent bond, O, S, SO, $SO_2$, $NR^2$, $NCOR^2$, $NCO_2R^2$, $NCNHR^2$ and $NSO_2R^2$, wherein $R^2$ is selected from hydrogen, alkyl, alkene, alkyne, heteroalkyl, haloalkyl, aryl, arylalkyl, heteroaryl, heteroarylalkyl, cycloalkyl, cycloalkylalkyl, heterocycloalkyl and heterocycloalkylalkyl; preferably Y is a covalent bond, O, S, $NR^2$, $NCOR^2$, $NCO_2R$ and $NSO_2R^2$. $R^2$ is preferably hydrogen, alkyl, heteroalkyl, aryl, or heteroaryl.

Z is selected from hydrogen, alkoxy, halogen, —CN, alkyl, alkene, alkyne, heteroalkyl, haloalkyl, aryl, arylalkyl, heteroaryl, heteroarylalkyl, cycloalkyl, cycloalkylalkyl, heterocycloalkyl, heterocycloalkylalkyl and acylated amino-acid residue. Alternatively, Z and $R^2$, together with the atoms to which they are bonded, join to form an optionally substituted heterocyclic ring containing from 5 to 8 atoms of which 1 to 3 are heteroatoms. Preferably, Z is aryl, arylalkyl, heteroaryl, heteroarylalkyl and acylated amino-acid residue. When Z and $R^2$ are bonded together, they preferably form a 5 or 6 membered ring with 1 or 2 heteroatoms.

G is selected from —S—, —O—, —N($R^3$)— and —CH=CH—, where $R^3$ is selected from hydrogen, alkyl, heteroalkyl and acyl; preferably G is —CH=CH— or —S—.

III. Compound Preparation:

The compounds of the invention can be prepared using a variety of procedures. The starting materials used in preparing the compounds of the invention are known, made by known methods, or are commercially available. Particularly preferred syntheses are described in the following general reaction schemes. (The R groups used to illustrate the reaction schemes do not necessarily correlate to the respective R groups used to describe the various aspects of the Formula (I) compounds. That is, for example, $R^1$ in Formula (I) does not represent the same moiety as $R^1$ here.) Specific examples for making the compounds of the present invention are set forth in Section IX, below:

of a Wittig reaction to provide a,b-unsaturated esters S1f bearing various substituents in the alpha position in respect to the ester group. When the $R_3$ group is chosen to be a benzyl group ester, S1f can be converted to the target carboxylic acid S1g using standard hydrogenolysis conditions and the palladium on carbon catalyst. If acid or base labile esters are used the corresponding hydrolysis conditions need to be applied after the hydrogenation of the double bond.

Scheme 2

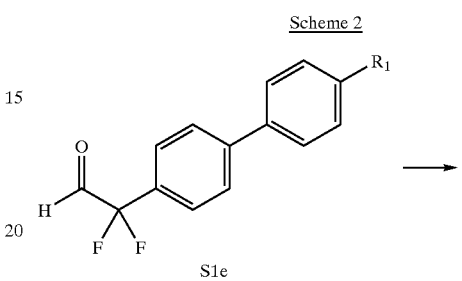

Scheme 1

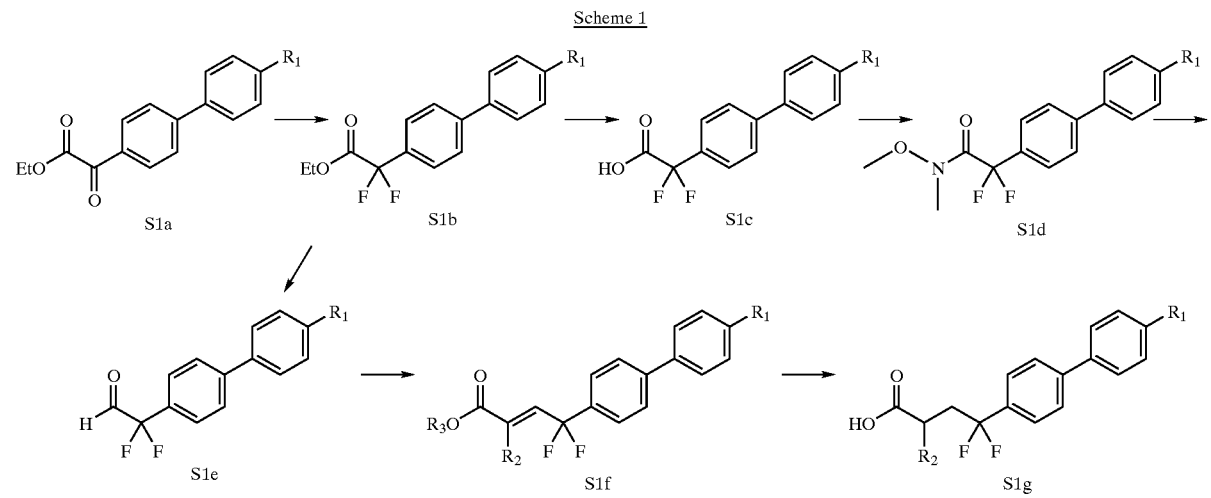

In Scheme 1, the ketoester S1a, easily prepared through the Friedel-Crafts reaction of the corresponding $R_1$ substituted biaryl substrate with oxalyl chloride monoethyl ester, can be treated with diethylaminosulfur trifluoride (DAST) to install a geminal difluoro-functionality in the alpha position of the ester group. The ester group of S1b can then be hydrolyzed using basic conditions and the resulting acid S1c can be converted to Weinreb amide S1d using standard literature coupling procedure. Amide S1d is then converted to aldehyde S1e upon reaction with lithium aluminum hydride. Alternatively, the aldehyde S1e can be prepared from ester S1b in a two-step reduction-oxidation sequence. First, lithium aluminum hydride can be used to perform reduction and the resulting intermediate alcohol is oxidized under the Swern oxidation conditions. The intermediate S1e of the invention is a subset of the useful intermediates of Formula (II). Aldehyde S1e can be homologated under the conditions -continued

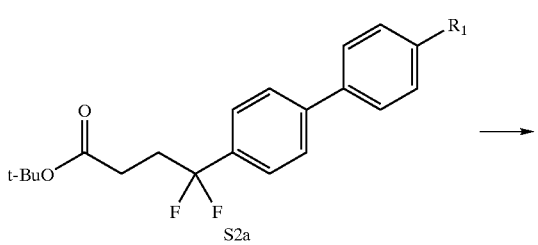

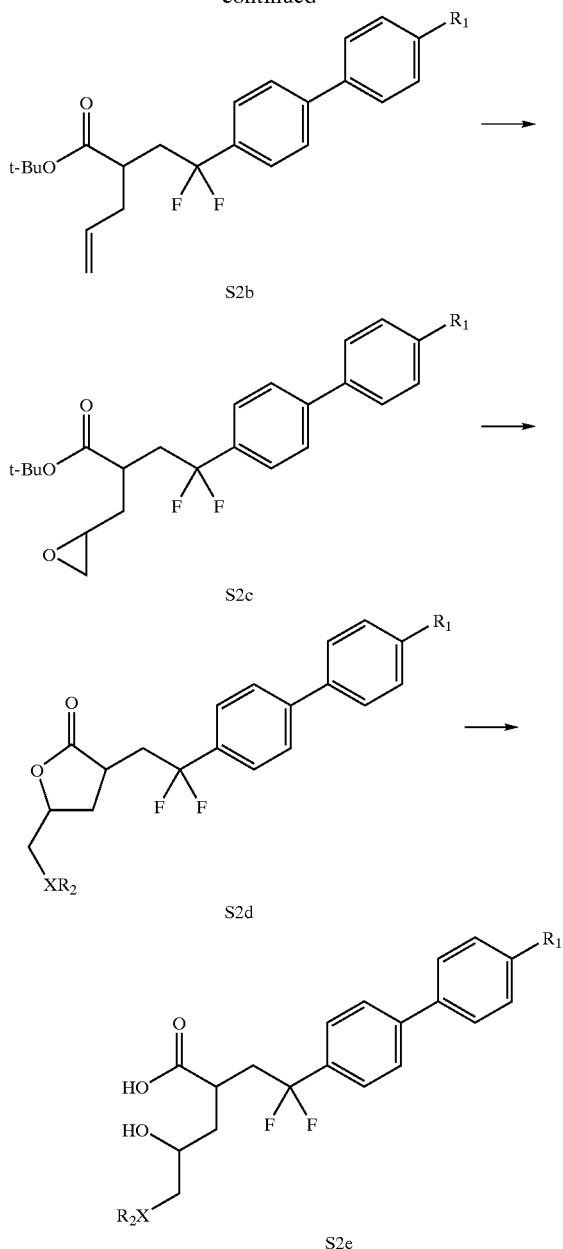

S2b

S2c

S2d

S2e

In Scheme 2, the aldehyde S1e is homologated as described above to give the t-butyl ester S2a. At this stage various substituents can be introduced at the alpha position in respect of the carbonyl group using standard alkylating conditions. Various alkylating agents can be used in this step. When allyl bromide is applied S2b can be obtained in good yield and the double bond can subsequently be functionalized to produce a key intermediate epoxide S2c. This material can be utilized as an electrophile in reactions with various sulfur-, nitrogen- or oxygen-based nucleophiles to give lactone S2d. Certain activating agents (e.g. boron trifluoride etherate or cesium carbonate) may need to be used to accelerate this transformation. The target carboxylic acids S2e are prepared from lactones S2d using the standard conditions of base promoted hydrolysis.

These steps may be varied to increase yield of desired product. The skilled artisan will recognize the judicious choice of reactants, solvents, and temperatures is an important component in any successful synthesis. Determination of optimal conditions, etc. is routine. Thus, the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

IV. Intermediates

The invention provides for novel chemistry for the synthesis of the compounds of Formula (I). This novel chemistry proceeds through the intermediates according to the following Formula (II).

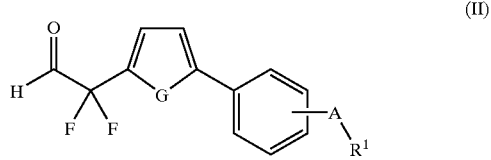

(II)

wherein

A is selected from a covalent bond, $C_1$–$C_3$ alkyl, O, S, SO and $SO_2$.

$R^1$ is selected from hydrogen, alkoxy, halogen, —CN, alkyl, alkene, alkyne, heteroalkyl, haloalkyl, aryl, arylalkyl, heteroaryl, heteroarylalkyl, cycloalkyl, cycloalkylalkyl, heterocycloalkyl and heterocycloalkylalkyl.

G is selected from —S—, —O—, —N(R$^3$)— and —CH=CH—, where R$^3$ is selected from hydrogen, alkyl, heteroalkyl and acyl.

The intermediates of Formula (II) are prepared according to Scheme 1, described in Section III, in which the intermediate of the invention is referred to as S1e.

V. Methods of Use:

Metalloproteases (MPs) found in the body operate, in part, by breaking down the extracellular matrix, which comprises extracellular proteins and glycoproteins. Inhibitors of metalloproteases are useful in treating diseases caused, at least in part, by the breakdown of such proteins and glycoproteins. These proteins and glycoproteins play an important role in maintaining the size, shape, structure and stability of tissue in the body. Thus, MPs are intimately involved in tissue remodeling.

As a result of this activity, MPs have been said to be active in many disorders involving either the: (1) breakdown of tissues including opthalmic diseases; degenerative diseases, such as arthritis, multiple sclerosis and the like; and metastasis or mobility of tissues in the body; or (2) remodeling of tissues including cardiac disease, fibrotic disease, scarring, benign hyperplasia, and the like.

The compounds of the present invention prevent or treat disorders, diseases and/or unwanted conditions which are characterized by unwanted or elevated activity by MPs. For example, the compounds can be used to inhibit MPs which:

1. destroy structural proteins (i.e. the proteins that maintain tissue stability and structure);
2. interfere in inter/intracellular signaling, including those implicated in cytokine up-regulation, and/or cytokine processing and/or inflammation, tissue degradation and other maladies [Mohler K M, et al, *Nature* 370 (1994) 218–220, Gearing A J H, et al, Nature 370 (1994) 555–557 McGeehan G M, et al, *Nature* 370 (1994) 558–561]; and
3. facilitate processes that are undesired in the subject being treated, for example, the processes of sperm maturation, egg fertilization and the like.

As used herein, an "MP related disorder" or "MP related disease" is one that involves unwanted or elevated MP activity in the biological manifestation of the disease or disorder; in the biological cascade leading to the disorder; or as a symptom of the disorder. This "involvement" of the MP includes:

1. The unwanted or elevated MP activity as a "cause" of the disorder or biological manifestation, whether the activity is elevated genetically, by infection, by autoimmunity, trauma, biomechanical causes, lifestyle [e.g. obesity] or by some other cause;
2. The MP as part of the observable manifestation of the disease or disorder. That is, the disease or disorder is measurable in terms of the increased MP activity. From a clinical standpoint, unwanted or elevated MP levels indicate the disease; however, MPs need not be the "hallmark" of the disease or disorder; or
3. The unwanted or elevated MP activity is part of the biochemical or cellular cascade that results or relates to the disease or disorder. In this respect, inhibition of the MP activity interrupts the cascade, and thus controls the disease.

The term "treatment" is used herein to mean that, at a minimum, administration of a compound of the present invention mitigates a disease associated with unwanted or elevated MP activity in a mammalian subject, preferably in humans. Thus, the term "treatment" includes: preventing an MP-mediated disease from occurring in a mammal, particularly when the mammal is predisposed to acquiring the disease, but has not yet been diagnosed with the disease; inhibiting the MP-mediated disease; and/or alleviating the MP-mediated disease. Insofar as the methods of the present invention are directed to preventing disease states associated with unwanted MP activity, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to MP-related disorders, such that administration of the compounds of the present invention may occur prior to onset of the disease. The term does not imply that the disease state be completely avoided. For example, osteoarthritis (OA) is the most common rheumatological disease with some joint changes radiologically detectable in 80% of people over 55 years of age. Fife, R. S., "A Short History of Osteoarthritis", *Osteoarthritis: Diagnosis and Medical/Surgical Management,* R. W. Moskowitz, D. S. Howell, V. M. Goldberg and H. J. Mankin Eds., p 11–14 (1992). A common risk factor that increases the incidence of OA is traumatic injury of the joint. Surgical removal of the meniscus following knee injury increases the risk of radiographically detectable OA and this risk increases with time. Roos, H et al. "Knee Osteoarthritis After Menisectomy: Prevalence of Radiographic Changes After Twenty-one Years, Compared with Matched Controls." *Arthritis Rheum.,* Vol. 41, pp 687–693; Roos, H et al. "Osteoarthritis of the Knee After Injury to the Anterior Cruciate Ligament or Meniscus: The Influence of Time and Age." *Osteoarthritis Cartilege,* Vol. 3, pp 261–267 (1995). Thus, this patient population is identifiable and could receive administration of a compound of the present invention before progression of the disease. Thus, progression of OA in such individuals would be "prevented".

Advantageously, many MPs are not distributed evenly throughout the body. Thus, the distribution of MPs expressed in various tissues are often specific to those tissues. For example, the distribution of metalloproteases implicated in the breakdown of tissues in the joints is not the same as the distribution of metalloproteases found in other tissues. Though not essential for activity or efficacy, certain diseases, disorders, and unwanted conditions preferably are treated with compounds that act on specific MPs found in the affected tissues or regions of the body. For example, a compound which displays a higher degree of affinity and inhibition for an MP found in the joints (e.g. chondrocytes) would be preferred for treatment of a disease, disorder, or unwanted condition found there than other compounds which are less specific.

In addition, certain inhibitors are more bioavailable to certain tissues than others. Choosing an MP inhibitor which is more bioavailable to a certain tissue and which acts on the specific MPs found in that tissue, provides for specific treatment of the disease, disorder, or unwanted condition. For example, compounds of this invention vary in their ability to penetrate into the central nervous system. Thus, compounds may be selected to produce effects mediated through MPs found specifically outside the central nervous system.

Determination of the specificity of an inhibitor of a specific MP is within the skill of the artisan in that field. Appropriate assay conditions can be found in the literature.

Specifically, assays are known for stromelysin and collagenase. For example, U.S. Pat. No. 4,743,587 references the procedure of Cawston, et al., *Anal Biochem* (1979) 99:340–345. See also, Knight, C. G. et al., "A Novel Coumarin-Labelled Peptide for Sensitive Continuous Assays of the Matrix Metalloproteases", *FEBS Letters*, Vol. 296, pp. 263–266 (1992). The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can be tested in the assays found in the literature, or variations thereof. Isolated metalloprotease enzymes can be used to confirm the inhibiting activity of the invention compounds, or crude extracts which contain the range of enzymes capable of tissue breakdown can be used.

The compounds of this invention are also useful for prophylactic or acute treatment. They are administered in any way the skilled artisan in the fields of medicine or pharmacology would desire. It is immediately apparent to the skilled artisan that preferred routes of administration will depend upon the disease state being treated and the dosage form chosen. Preferred routes for systemic administration include administration perorally or parenterally.

However, the skilled artisan will readily appreciate the advantage of administering the MP inhibitor directly to the affected area for many diseases, disorders, or unwanted conditions. For example, it may be advantageous to administer MP inhibitors directly to the area of the disease, disorder, or unwanted condition such as in the area affected by surgical trauma (e.g., angioplasty), scarring, burning (e.g., topical to the skin), or for opthalmic and periodontal indications.

Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In one aspect of the present invention, the compounds of Formula I of the present invention may be effective in preventing or treating myocardial infarction (hereinafter "MI"). MI, also known as a "heart attack" or "heart failure," is a condition caused by partial or complete occlusion of one or more of the coronary arteries, usually due to rupture of an atherosclerotic plaque. The occlusion of the coronary artery results in cardiac ischemia. MMPs are implicated in artherosclerotic plaque rupture. See e.g., Galis, Z. S., et al., J. Clin. Invest. 1994;94:2493–503; Lee, R. T., et al., Arterioscler.Thromb.Vasc.Biol. 1996;16:1070–73; Schonbeck, U. et al., Circulation Research 1997; 81(3), 448–454. Libby, P. et al., Circ. 1995;91:2844–50.

In another aspect of the invention, the compounds of the present invention may be effective in preventing or treating progressive ventricular dilation after a MI, the major contributing factor to the development of post-MI chronic heart failure (hereinafter "CHF"). Thus, in yet still another aspect of the invention, the compounds of the present invention may be effective in preventing or treating the development of post-MI chronic heart failure.

It is widely recognized that important structural changes occur within the ventricular myocardium following MI that results in alterations in LV geometry and function. These structural alterations occur in the infarct itself, in the border zone of the MI, and in regions remote from the MI that collectively result in progressive ventricular dilation and pump dysfunction. The most notable feature of this remodeling process is the region of the original MI appears to enlarge with thinning of the ventricular myocardial wall. This type of remodeling following the initial injury and healing process from an MI has been termed "infarct expansion." A significant body of work suggests that treatment of acute myocardial infarction with an MMP inhibitor will limit the unfavorable dilation of the heart that occurs early after such an event and therefore improve outcomes by preventing long-term sequelae, such as the development of chronic heart failure. See, e.g., Spinale, F. G. et al., Circulation Research 82:482–495 (1998); McElmurray, J. H. I. et al., J. Pharmacol. Exp. Ther. 291:799–811 (1999); Thomas, C. V. et al., Circulation 97:1708–1715 (1998); Spinale, F. G. et al. Circ. 102:1944–49 (2000); Peterson, J. T. et al., Cardiovasc. Res., 46(2):307–15 (2000); Rohde, L. E. et al., Circ., 99:3063–70 (1999); Lindsey, M. L. et al., Circ 105:753–58 (2002); Brinsa, T. A. et al., J. Cardiac Failure, 7 Suppl. 2:24 (2001); Mukherjee, R. et al., J. Cardiac Failure; 7 Suppl 2:7 (2001).

A suitable MI cardiac pharmacological model is described in Mukherjee, R. et al., J. Cardiac Failure; 7 Suppl 2:7 (2001). Briefly, pigs are prepared for the induction of myocardial infarction by implantation of an occlusion device on the circumflex coronary artery, and radiopaque markers are placed in the region destined to be infarcted to measure infarct expansion (see below). Measurements of left ventricular (hereinafter "LV") volumes and distances between marker beads are made prior to and at various times after the induction of MI induced by activating the occlusion device.

The effects of selective MMP inhibition may be studied in a pig model of MI induced by ligation of the circumflex coronary artery. Animals are assigned to one of the following treatment groups: (1) 1 or 10 mg/kg three times a day of a compound of Formula (I) by oral administration starting 3 days prior to myocardial infarction; (2) 10 mg/kg three times a day of said compound by oral administration starting 3 days after MI; (3) MI with no active treatment; or (4) no myocardial infarction or drug treatment. At 10 days post-MI, LV end-diastolic volume (hereinafter "LVEDV") is measured by ventriculography. LVEDV is increased in all MI groups. An attenuated increase in LVEDV by a compound of Formula (I) indicates that the compound may be effective in the prevention or treatment of progressive ventricular dilation, and thus the subsequent development of CHF.

In skin care, MPs are implicated in the remodeling or "turnover" of skin. As a result, the regulation of MPs improves treatment of skin conditions including, but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultraviolet damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly, in diseases such as multiple sclerosis, MPs may be involved in the irregular modeling of blood brain barrier and/or myelin sheaths of nervous tissue. Thus, regulating MP activity may be used as a strategy in treating, preventing, and controlling such diseases.

MPs are also thought to be involved in many infections, including cytomegalovirus (CMV); retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

Additionally, they are also contemplated to be useful in preventing or stopping premature labor and delivery.

Since MPs are implicated in the inflammatory response and in the processing of cytokines, the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythematosus, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis and acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives.

For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and regulation of hair growth.

For some diseases, conditions or disorders MP inhibition is contemplated to be a preferred method of treatment. Such diseases, conditions or disorders include, arthritis (including osteoarthritis and rheumatoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the matrix metalloproteases and the disintegrin metalloproteases. Compounds preferred for, but not limited to, the treatment of cancer (especially the prevention or arrest of tumor growth and metastasis) are those compounds that preferentially inhibit gelatinases or type IV collagenases. Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel. Compounds preferred for, but not limited to, the treatment of gum disease (especially periodontal disease, and gingivitis) are those compounds that preferentially inhibit collagenases.

VI. Compositions:

The compositions of the invention comprise:

(a) a safe and effective amount of a compound of the invention; and (b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective to inhibit metalloproteases at the site(s) of activity in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated. The choice of a pharmaceutically-acceptable carrier to be used in conjunction with the subject compound is determined in-part by the way the compound is to be administered.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween®; wetting agents, such sodium lauryl sulfate; coloring agents; flavoring agents; tableting agents; stabilizers; antioxidants; preservatives; pyrogen-free water; isotonic saline; and phosphate buffer solutions.

Pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition. If the subject compound is to be injected, the preferred pharmaceutically-acceptable carrier is sterile, physiological saline, with a blood-compatible suspending agent, the pH of which has preferably been adjusted to about 7.4.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, and can contain suitable binders, lubricants, diluents, disintegrating agents, coloring agents, flavoring agents, flow-inducing agents, and/or melting agents. Liquid oral dosage forms include aqueous solutions, emulsions, suspensions, solutions and/or suspensions reconstituted from non-effervescent granules, and effervescent preparations reconstituted from effervescent granules. Such liquid dose forms will optionally contain suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents such as calcium carbonate, sodium carbonate, mannitol, lactose and cellulose; binders such as starch, gelatin and sucrose; disintegrants such as starch, alginic acid and croscarmelose; and lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as the sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

VII. Methods of Administration:

This invention also provides methods of treating disorders associated with excess or undesired metalloprotease activity in a human or other animal subject, by administering a safe and effective amount of a Formula (I) compound to said subject. As used herein, a "disorder associated with excess or undesired metalloprotease activity" is any disorder characterized by degradation of matrix proteins. The methods of the invention are useful in treating disorders described above.

As indicated, compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of compound to be administered, as well as the duration of treatment and whether the treatment is topical or systemic, are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenteral dosing via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The compounds of the invention can be targeted to specific locations where the metalloprotease is accumulated by using targeting ligands. For example, to direct the compounds to metalloproteases contained in a tumor, the compound is conjugated to an antibody or fragment thereof which is immunoreactive with a tumor marker, as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carriers. The conjugates are formulated and administered as described below.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically in a gel, paste, salve or ointment. For treatment of oral diseases, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases. Some bacterial metalloproteases may be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

VIII. Preparation and Use of Antibodies:

Metalloproteases active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples of Sections IX and X illustrate the compounds, compositions, and methods of the present invention.

IX. EXAMPLES

Compound Preparation

Typically tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merk) as appropriate. Thin layer chromatography analysis (TLC) is performed on glass mounted silica gel plates (200–300 mesh; Baker) and visualized with UV or 5% phosphomolybdic acid in ethanol (EtOH).

The following abbreviations are used herein:

| | | | |
|---|---|---|---|
| MeOH: | methanol | RT: | room temperature |
| EtOAc: | ethylacetate | THF: | tetrahydrofuran |
| Ph: | phenyl | mp: | melting point |
| equiv: | equivalents | aq: | aqueous |
| min: | minute | | |

The R groups used to illustrate the compound examples do not correlate to the respective R groups used to describe the various moieties of Formula (I). That is, for example, $R^1$ used to describe Formula (I) in the Summary of the Invention section and Section II of the Detailed Description do not represent the same moiety as $R_1$ in this Section IX.

Examples 1–17

The following chart shows the structure of compounds made according to the procedures described in Examples 1–17.

| Example | $R_1$ | $R_2$ |
|---|---|---|
| 1 | —H | —OMe |
| 2 | —Me | —OMe |
| 3 | —Et | —OMe |
| 4 | —Pr | —OMe |
| 5 | —CH$_2$Ph | —H |
| 6 | —CH$_2$Ph | —OMe |
| 7 | —CH$_2$Ph | —OEt |
| 8 | —CH$_2$Ph | —OCH$_2$CH$_2$OMe |
| 9 | —CH$_2$Ph | —F |
| 10 | —CH$_2$Ph | —Cl |
| 11 | —CH$_2$-2-pyridyl | —OMe |
| 12 | —CH$_2$-3-pyridyl | —OMe |
| 13 | —CH$_2$-4-pyridyl | —OMe |
| 14 | —CH$_2$-2-furfuryl | —OMe |
| 15 | —CH$_2$-3-indolyl | —OMe |
| 16 | —CH$_2$CH$_2$Ph | —OMe |
| 17 | —CH$_2$CH$_2$CH$_2$Ph | —OMe |

Example 1

4,4-Difluoro-4-(4'-methoxy-biphenyl-4-yl)-butyric Acid.

(a) Difluoro-(4'-methoxy-biphenyl-4-yl)-acetic acid ethyl ester. Diethylaminosulfur trifluoride (5 mL) is added directly to (4'-methoxy-biphenyl-4-yl)-oxo-acetic acid ethyl ester (3.77 g, 13.3 mmol), prepared as described by Neidlin, et. al., Arzneim.-Forsch. 1983, 33, 691–3. Dichloromethane (2 mL) is added and the mixture is stirred overnight at room temperature. The reaction is diluted with dichloromethane and slowly added to ice water. This mixture is extracted with ethyl acetate twice. The combined organic extracts are dried over Na$_2$SO$_4$, filtered, and concentrated under reduced pressure. The crude product is purified by column chromatography (silica gel, 5% EtOAc/hexanes) to give the desired product as a pale yellow solid.

(b) Difluoro-(4'-methoxy-biphenyl-4-yl)-acetic acid. To a solution of difluoro-(4'-methoxy-biphenyl-4-yl)-acetic acid ethyl ester (2.30 g, 7.51 mmol) in methanol (150 mL) is added 1.0 N aq. NaOH (16.5 mL, 16 mmol). During this addition, the reaction becomes cloudy and then clear again. The reaction is acidified to pH 5 with 1.0 N aq. HCl and diluted with water. NaCl is added and the mixture is extracted with ethyl acetate four times. The combined organic extracts are washed with brine, dried over Na$_2$SO$_4$, filtered, and concentrated under reduced pressure to give the crude product as a white solid.

(c) 2,2-Difluoro-N-methoxy-2-(4'-methoxy-biphenyl-4-yl)-N-methyl-acetamide. To a solution of difluoro-(4'-methoxy-biphenyl-4-yl)-acetic acid (3.74 g, 13.4 mmol) in dichloromethane (40 mL) and acetonitrile (40 mL) is added oxalyl chloride (2.40 mL, 27.5 mmol) followed by N,N-dimethylformamide (1.05 mL, 13.6 mmol). This mixture is stirred at room temperature for 45 min and added over 10 min to a solution of N,O-dimethylhydroxylamine hydrochloride (5.23 g, 53.6 mmol) and triethylamine (11.2 mL, 80.4 mmol) in t-butanol (40 mL), THF (80 mL), and water (30 mL) at 0° C. The resulting mixture is stirred for 4 hours while warming from 0° C. to room temperature. The reaction is diluted with water and the layers separated. The organic layer is washed in succession with saturated aqueous NaHCO$_3$ and brine, dried over Na$_2$SO$_4$, filtered, and concentrated under reduced pressure. The crude product is purified by column chromatography (silica gel, 20–30% EtOAc/hexanes) to give the desired product as a pale yellow solid.

(d) Difluoro-(4'-methoxy-biphenyl-4-yl)-acetaldehyde. To a solution of 2,2-difluoro-N-methoxy-2-(4'-methoxy-biphenyl-4-yl)-N-methyl-acetamide (3.60 g, 11.2 mmol) in THF (100 mL) at −40° C. is added 1.0 M lithium aluminum hydride in THF (12 mL, 12 mmol). This mixture is stirred under argon for 6 hours while warming to room temperature. The reaction is quenched slowly with excess 1.0 N aq. HCl and extracted with diethyl ether three times. The combined organic extracts are dried over Na$_2$SO$_4$, filtered, and concentrated under reduced pressure to give the crude product as an off-white solid. The crude product is used as is with no purification.

(e) 4,4-Difluoro-4-(4'-methoxy-biphenyl-4-yl)-but-2-enoic acid ethyl ester. A solution of benzyl (triphenylphosphoranylidene)acetate (320 mg, 0.779 mmol) and 2,2-difluoro-2-(4'-methoxy-4-biphenyl)acetaldehyde (198 mg, 0.755 mmol) in toluene (4 mL) is heated to 90° C. with stirring for 2 hours. The reaction is cooled to room temperature and concentrated under reduced pressure. The crude product is purified by column chromatography (silica gel, 20% EtOAc/hexanes) to give the desired product as a pale yellow oil.

(f) 4,4-Difluoro-4-[4'-methoxy-4-biphenyl]butanoic acid. A mixture of 4,4-difluoro-4-(4'-yl)-but-2-enoic acid benzyl ester (214 mg, 0.543 mmol) and 10% palladium on activated carbon (195 mg) in ethyl acetate (10 mL) is stirred overnight under hydrogen at room temperature. The reaction is filtered and the filtrate concentrated under reduced pressure. The crude product is purified by reverse phase preparative HPLC (gradient elution, 0.1% aq. trifluoroacetic acid/acetonitrile) to give the desired product as a white solid.

Examples 2–4

Examples 2–4 are prepared following the procedure described for Example 1 using the corresponding Wittig reagent in step 1e.

Examples 5–10

Examples 5–10 are prepared following the procedure described for Example 1 using appropriately substituted biphenyl oxo-acetic acid ethyl ester in step 1a and 3-phenyl-2-(triphenylphosphanylidene)-propionic acid benzyl ester in step 1e.

Examples 11–17

Examples 11–17 are prepared following the procedure described for Example 1 using the corresponding Wittig reagent in step 1e.

Examples 18–29

The following chart shows the structure of compounds made according to the procedures described in Examples 18–29.

| Example | R$_1$ | R$_2$ |
|---|---|---|
| 18 | —Ph | —OMe |
| 19 | benzothiazol-2-yl | —OMe |
| 20 | 4,5-dihydrothiazol-2-yl | —OMe |
| 21 | pyridin-2-yl | —OMe |
| 22 | benzyl | —OMe |
| 23 | 1-methylimidazol-2-yl | —OMe |
| 24 | 1-phenylimidazol-2-yl | —OMe |
| 25 | 4-chlorophenyl | —OMe |
| 26 | HO$_2$C—CH(NHAc)—CH$_2$— | —OMe |
| 27 | —Ph | —OEt |
| 28 | —Ph | —OCH$_2$CH$_2$OMe |
| 29 | —Ph | —F |

Example 18

2-[2,2-Difluoro-2-(4'-methoxy-biphenyl-4-yl)-ethyl]-4-hydroxy-5-phenylsulfanyl-pentanoic acid.

(a) 4,4-Difluoro-4-(4'-methoxy-biphenyl-4-yl)-but-2-enoic acid tert-butyl ester. To a solution of Example 1d (20 mmol) in benzene (150 mL) is added (t-butoxycarbonylmethylene)-triphenylphosphorane (7.90 g, 21 mmol) and the resulting mixture is refluxed for 2 hours. The mixture is concentrated and the crude product is purified by silica gel column chromatography (hexane-ethyl acetate 6:1) to give the desired product as a white solid. Recrystallization from hexane provides the product as colorless needles: mp 110–111° C.

(b) 4,4-Difluoro-4-(4'-methoxy-biphenyl-4-yl)-butyric acid tert-butyl ester. To a solution of Example 18a (1.80 g, 5 mmol) in ethyl acetate (100 mL) is added 5% Pd on sulfide carbon (180 mg) and the mixture is stirred under hydrogen atmosphere at RT for 6 hours. Filtration through a plug of Celite and concentration gives the crude material which is purified by crystallization from hexane to give the desired product as colorless needles: mp 85–86° C.

(c) 2-[2,2-Difluoro-2-(4'-methoxy-biphenyl-4-yl)-ethyl]-pent-4-enoic acid tert-butyl ester. To a solution of sodium bis(trimethylsilyl)amide (3 mL, 2M in THF, 6 mmol) in THF (27 mL) cooled to −78° C. is added dropwise over 15 min a solution of Example 18b (1.60 g, 4.42 mmol) in dry THF (20 mL). After an additional 0.5 hours at −78° C., allyl bromide (968 mg, 8 mmol) is added and the mixture is allowed to warm to −10° C. over 0.5 hours. The reaction is quenched with 1N HCl and extracted with ether. The combined organic layers are washed with saturated NaHCO3, water, brine, dried over MgSO4, filtered and concentrated. The crude material is purified by flash chromatography (6/1 hexane/EtOAc) and recrystallized from hexane to give the desired product as colorless needles: mp 55–56° C.

(d) 4,4-Difluoro-4-(4'-methoxy-biphenyl-4-yl)-2-oxiranylmethyl-butyric acid tert-butyl ester. To a solution of Example 18c (1.40 g, 3.48 mmol) in dichloromethane (40 mL), cooled to 0° C., is added meta-chloroperbenzoic acid (12.5 mmol, 3.6 equiv). The mixture is allowed to warm to room temperature and then is stirred for 24 hours. Saturated $Na_2CO_3$ aq. (40 mL) is added and the mixture is stirred for 0.5 hour. The organic layer is separated and the aqueous layer is extracted with ethyl acetate. The combined organic layers are washed with brine, dried over $MgSO_4$, filtered and concentrated. The crude material is purified by flash chromatography (4/1 hexane/acetone) and recrystallized from hexane/acetone to give the desired compound as colorless needles: mp 70–71° C.

(e) 3-[2,2-Difluoro-2-(4'-methoxy-biphenyl-4-yl)-ethyl]-5-phenylsulfanylmethyl-dihydro-furan-2-one. A solution of phenylthiol (0.65 mmol) in THF (5 mL) is treated with BuLi (0.65 mmol) at −20° C. After being stirred for 20 min at −20° C., Example 18d (0.5 mmol) in THF (5 mL) is added dropwise. The mixture is allowed to warm to 0° C. and kept at that temperature for 2 hours, then is warmed up to room temperature and stirred for 3 hours. The reaction is quenched with saturated $NH_4Cl$, neutralized with 1N HCl and extracted with ethyl acetate. The combined organic layers are washed with brine and dried over $MgSO_4$. The crude material obtained after evaporation of solvents is purified by flash chromatography (3/1 hexane/acetone) and recrystallized from hexane/acetone to give the desired compound as colorless needles: mp 117–118° C.

(f) 2-[2,2-Difluoro-2-(4'-methoxy-biphenyl-4-yl)-ethyl]-4-hydroxy-5-phenylsulfanyl-pentanoic acid. A mixture of Example 18e (0.3 mmol) in 1% KOH/MeOH (1.85 mL, 0.33 mmol) is stirred at room temperature for 2 hours. The white solids are collected and washed with cold methanol to give the desired compound as a potassium salt: mp 134–136° C.

Examples 19–26

Examples 19–26 are prepared following the procedure described for Example 18 using the corresponding thiol in step 18e.

Examples 27–29

Examples 27–29 are prepared following the procedure described for Example 18 using appropriately substituted difluoro-biphenyl-acetaldehyde in step 18a.

X. EXAMPLES

Compositions and Methods of Use

The compounds of the invention are useful to prepare compositions for the treatment of ailments associated with unwanted MP activity. The following composition and method examples do not limit the invention, but provide guidance to the skilled artisan in preparing and using the compounds, compositions and methods of the invention. In each case, other compounds within the invention may be substituted for the example compound shown below to provide substantially similar results. The skilled practitioner will appreciate that the examples provide guidance and may be varied based on the condition being treated and the patient.

The following abbreviations are used:

EDTA: ethylenediaminetetracetic acid

SDA: synthetically denatured alcohol

USP: United States Pharmacopoeia

Example A

A tablet composition for oral administration, according to the present invention, is made comprising:

| Component | Amount |
| --- | --- |
| The compound of Example 1 | 15 mg |
| Lactose | 120 mg |
| Maize Starch | 70 mg |
| Talc | 4 mg |
| Magnesium Stuart | 1 mg |

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation and improved mobility without concomitant pain.

Example B

A capsule for oral administration, according to the present invention, is made comprising:

| Component | Amount (% w/w) |
| --- | --- |
| The compound of Example 6 | 15% |
| Polyethylene glycol | 85% |

A human male subject weighing 90 kg (198 lbs.), suffering from osteoarthritis, is treated by a method of this invention. Specifically, for 5 years, the above capsule, which contains 70 mg of the compound of Example 4, is administered daily to said subject.

At the end of the treatment period, the patient is examined via x-ray, arthroscopy and/or MRI, and found to have no further advancement of erosion/fibrillation of the articular cartilage.

Example C

A saline-based composition for local administration, according to the present invention, is made comprising:

| Component | Amount (% w/w) |
|---|---|
| The compound of Example 8 | 5% |
| Polyvinyl alcohol | 15% |
| Saline | 80% |

A patient having deep corneal abrasion applies a drop of the composition to each eye twice a day. Healing is speeded, with no visual sequelae.

Example D

A topical composition for local administration, according to the present invention, is made comprising:

| Component | Composition (% w/v) |
|---|---|
| The compound of Example 10 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

A patient suffering from chemical burns applies the composition at each dressing change (b.i.d.). Scarring is substantially diminished.

Example E

An inhalation aerosol composition, according to the present invention, is made comprising:

| Component | Composition (% w/v) |
|---|---|
| Compound of Example 13 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

An asthma sufferer sprays 0.01 mL of the composition via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 16 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

A human male subject weighing 90 kg (198 lbs), suffering from corneal ulcerations, is treated by a method of this invention. Specifically, for 2 months, a saline solution containing 10 mg of the compound of Example 16 is administered to said subject's affected eye twice-daily.

Example G

A composition for parenteral administration is made comprising:

| Component | Amount |
|---|---|
| The compound of Example 12 | 100 mg/mL carrier |
| Carrier: | |
| Sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 mL of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Example H

A mouthwash composition is prepared:

| Component | % w/v |
|---|---|
| The compound of Example 14 | 3.0 |
| SDA 40 Alcohol | 8.0 |
| Flavor | 0.08 |
| Emulsifier | 0.08 |
| Sodium Fluoride | 0.05 |
| Glycerin | 10.0 |
| Sweetener | 0.02 |
| Benzoic acid | 0.05 |
| Sodium hydroxide | 0.20 |
| Dye | 0.04 |
| Water | balance to 100% |

A patient with gum disease uses 1 mL of the mouthwash thrice daily to prevent further oral degeneration.

Example I

A lozenge composition is prepared:

| Component | % w/v |
|---|---|
| The compound of Example 18 | 0.01 |
| Sorbitol | 17.50 |

-continued

| Component | % w/v |
|---|---|
| Mannitol | 17.50 |
| Starch | 13.60 |
| Sweetener | 1.20 |
| Flavor | 11.70 |
| Color | 0.10 |
| Corn Syrup | balance to 100% |

A patient uses the lozenge to prevent loosening of an implant in the maxilla.

Example J

A chewing gum composition is prepared, comprising the following:

| Component | w/v % |
|---|---|
| The compound of Example 20 | 0.03 |
| Sorbitol crystals | 38.44 |
| Paloja-T gum base | 20.0 |
| Sorbitol (70% aqueous solution) | 22.0 |
| Mannitol | 10.0 |
| Glycerine | 7.56 |
| Flavor | 1.0 |

A patient chews the gum to prevent loosening of dentures.

Example K

| Components | w/v % |
|---|---|
| Compound of Example 28 | 4.0 |
| USP Water | 50.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

The composition is prepared by first mixing 80 kg of glycerin and all of the benzyl alcohol and heating to 65° C., then slowly adding and mixing together methylparaben, propylparaben, water, xanthan gum, and guar gum. These ingredients are mixed for about 12 minutes with a Silverson in-line mixer. The following ingredients then added in the following order: remaining glycerin, sorbitol, antifoam C, calcium carbonate, citric acid, and sucrose. The flavors and coolants are separately combined and then are slowly added to the other ingredients. The mixture is mixed for about 40 minutes. The patient takes the formulation to prevent flare up of colitis.

Example L

An obese human female subject, who is determined to be prone to osteoarthritis, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

Example M

A human male subject weighing 90 kg (198 lbs.), who suffers a sports injury, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to formula (I):

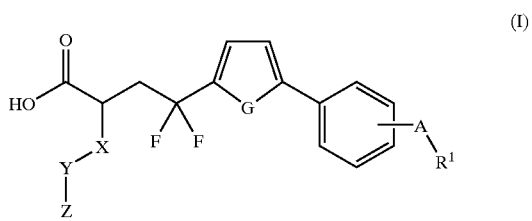

wherein:

(A) A is selected from a covalent bond, $C_1$–$C_3$ alkyl, O, S, SO, and $SO_2$;

(B) $R^1$ is selected from hydrogen, alkoxy, halogen, —CN, alkyl, alkene, alkyne, haloalkyl, aryl, arylalkyl, cycloalkyl, and cycloalkylalkyl;

(C) X is selected from a covalent bond and $C_1$–$C_3$ alkyl optionally substituted with a hydroxy group;

(D) Y is selected from a covalent bond;

(E) Z is selected from 3-indolyl; and (F) G is selected from —S—, —O—, —N($R^3$)— and —CH=CH—, where $R^3$ is selected from hydrogen, alkyl, and acyl;

or an optical isomer, diasteromer or enantiomer for Formula (I), or a pharmaceutically-acceptable salt, or biohydrolyzable ester thereof or conjugates thereof.

2. The compound according to claim 1 wherein G is —CH=CH— or —S—.

3. The compound according to claim 1 wherein A is covalent bond, O or S.

4. The compound according to claim 3 wherein A is O or S.

5. The compound according to claim 1 wherein $R^1$ is hydrogen, alkyl, or halogen.

6. The compound according to claim 1, wherein the compound is:

4,4-Difluoro-2-(1H-indol-2-ylmethyl)-4-(4'-methoxy-biphenyl-4-yl)-butric acid.

7. A pharmaceutical composition comprising:

(a) a safe and effective amount of a compound of claim 1; and (b) a pharmaceutically-acceptable carrier.

* * * * *